United States Patent [19]
Lee

[11] Patent Number: 5,579,762
[45] Date of Patent: Dec. 3, 1996

[54] ENDOTRACHEAL DEVICE TO FACILITATE JOINING AN ENDOTRACHEAL TUBE TO AN ADAPTOR CONNECTED TO A SUCTION OR GAS SOURCE

[76] Inventor: Cindy Lee, 9120 Hoffman Farm La., Cincinnati, Ohio 45242

[21] Appl. No.: 509,783

[22] Filed: Aug. 1, 1995

[51] Int. Cl.$^6$ ................................................. A61M 16/00
[52] U.S. Cl. ............................... 128/207.14; 128/200.24; 128/912; 285/246
[58] Field of Search ........................ 128/202.27, 207.14, 128/200.24, 912; 285/246, 247

[56] References Cited

U.S. PATENT DOCUMENTS

| 4,437,689 | 3/1984 | Goebel et al. ............................. 285/246 |
| 4,846,167 | 7/1989 | Tibbals ................................ 128/202.27 |
| 5,258,015 | 11/1993 | Li et al. .................................... 606/232 |
| 5,285,776 | 2/1994 | Bertram .............................. 128/207.14 |

FOREIGN PATENT DOCUMENTS

| 129589 | 8/1945 | Australia ................................ 285/246 |
| 94903 | 6/1922 | Switzerland ........................... 285/246 |
| 353 | 10/1852 | United Kingdom .................... 285/246 |
| 23199 | 10/1902 | United Kingdom .................... 285/246 |
| 181280 | 6/1922 | United Kingdom .................... 285/246 |

*Primary Examiner*—V. Miller
*Assistant Examiner*—Eric P. Raciti
*Attorney, Agent, or Firm*—Wood, Herron & Evans, P.L.L.

[57] ABSTRACT

An endotracheal device to facilitate joining an endotracheal tube to an adaptor connected to a suction or gas source is disclosed. The device is a tubular connector having opposed ends, one end of which has a locking means for temporarily locking the connector to the adaptor and another end for receiving and securing the tube to the connector.

4 Claims, 1 Drawing Sheet

ENDOTRACHEAL DEVICE TO FACILITATE JOINING AN ENDOTRACHEAL TUBE TO AN ADAPTOR CONNECTED TO A SUCTION OR GAS SOURCE

FIELD OF THE INVENTION

This invention generally relates to an endotracheal device that facilitates securely joining an endotracheal tube to an adaptor connected to a gas or suction source to prevent the disjunction of the source from the tube.

BACKGROUND OF THE INVENTION

During various medical procedures, it is often necessary to insert an endotracheal tube into a patient for such purposes as administering anesthesia. Generally, the prior art tube is connected to an endotracheal tube adaptor, which in turn, is connected to a gas source. Typically, the adaptor has a tubular first end that slides partially in a first end of the endotracheal tube to form a telescoping connection (more commonly known as a male-female connection) therebetween. The adaptor has a second end portion adapted to receive and secure a gas source. A danger exists that the endotracheal tube and adaptor will become disconnected as the tubular first end of the adaptor can easily slide out of the first end of the tube. For example, if such disconnection occurs while the tube and adaptor are in a patient, the source will in turn become disconnected from the patient resulting in the interruption of oxygen and/or anesthesia and the possibility of harm to the patient. In other instances when the endotracheal tube is used for suctioning or lavaging the lungs, such an interruption can be threatening to the well being of the patient. Also, when the tube becomes disconnected from the adaptor, the adaptor often becomes lost as it may fall on the floor or on the operating table, thereby making it impossible to reconnect the source to the patient.

Accordingly, it is a primary objective of this invention to provide an endotracheal device that facilitates securely joining an endotracheal tube to an adaptor connected to a source without the risk of the source becoming disconnected while the tube is within a patient.

BRIEF SUMMARY OF THE INVENTION

This invention provides an endotracheal device that facilitates joining an endotracheal tube to an adaptor connected to a suction or gas source. The endotracheal device is comprised of a tubular ring or connector having opposed ends. One end of the connector has a locking means for temporarily locking the connector to the adaptor, that is, in turn, connected to the source. Another end of the connector is adapted to facilitate securement to an endotracheal tube.

In a preferred form, one end of the connector having the locking means is threaded for temporarily engaging the connector to a cooperatively threaded end of an adaptor, which is connected to the source. The opposed end of this embodiment is adapted for interference fit with the endotracheal tube. More specifically, the endotracheal tube is sandwiched or trapped between the outside of the end of the adaptor and the inside of the opposed, nonthreaded end of the connector. In the preferred form, the connector slides up and down the endotracheal tube when it is not locked to the adaptor. This facilitates adjustment of the tube length by cutting off an end and then sliding the tubular connector for locking engagement with the adaptor and interference fit with the tube.

In another subsidiary aspect of the invention, the connector may have flanges extending generally perpendicularly from an exterior surface of the connector to facilitate grasping and twisting of the connector.

DETAILED DESCRIPTION OF PREFERRED EMBODIMENT

Figure 1:
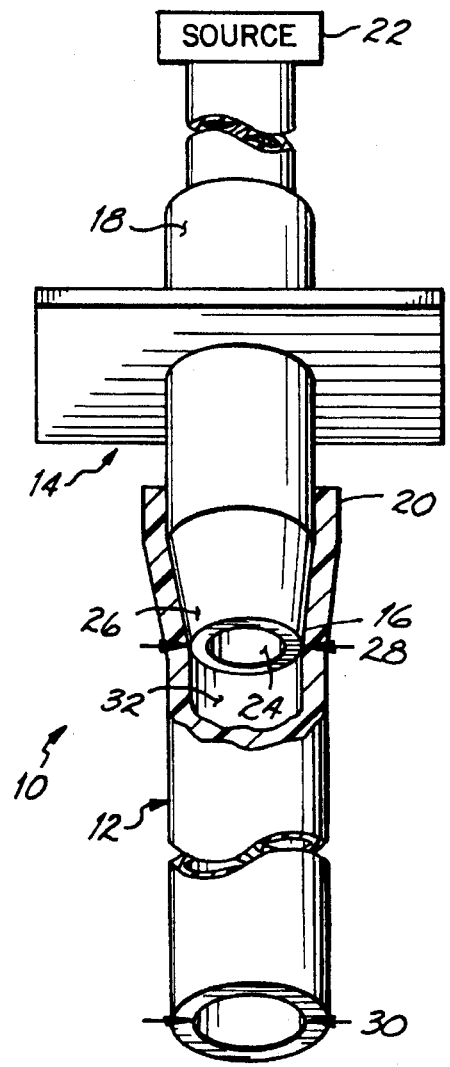
FIG. 1 is a perspective view of an endotracheal system of the prior art.

FIG. 1 represents an endotracheal system 10 of the prior art. System 10 is comprised of an endotracheal tube 12 and an endotracheal tube adaptor 14. Adaptor 14 has a first end 16 and a second end 18, with first end 16 being connected to tube 12 and second end 18 being connected to a source 22 of gas, suction or the like. Both tube 12 and adaptor 14 are generally comprised of a plastic material.

First end 16 of adaptor 14 is tubular shaped having a generally smooth inner surface 24 and outer surface 26, and adapted to connect to tube 12 via a telescoping connection, more commonly known as a male-female connection. More particularly, first end 16 of adaptor 14 is tapered having a slightly smaller diameter 28 than the diameter 30 of first end 20 of tube 12 so that tapered first end 16 of adaptor 14 slides in first end 20 of tube 12 to the extent of the taper and is held in position by friction between the inner surface 32 of tube 12 and outer surface 26 of adaptor 14.

Although tube 12 and adaptor 14 are held in position by friction, it is fairly simple for tube 12 and adaptor 14 to slide apart and become completely disengaged during a medical procedure. Often the adaptor 14 falls onto the ground or on the operating table (not shown) when disengagement occurs and cannot be found, making re-engagement of adaptor 14 and tube 12 impossible. Disengagement of tube 12 and adaptor 14 is dangerous since adaptor 14 is in turn, typically connected to the patient's gas or anesthetic source 22. Thus, if tube 12 and adaptor 14 become disconnected from each other, oxygen and/or anesthesia will, in turn, become disconnected from the patient. Similarly, if tube 12 is being used to suction the lungs of a patient and becomes disconnected from adaptor 14, the well being of the patient will be at risk. It is therefore critical that source 22 not become disconnected from system 10 while endotracheal tube 12 is within the trachea of the patient (not shown).

Figure 2:
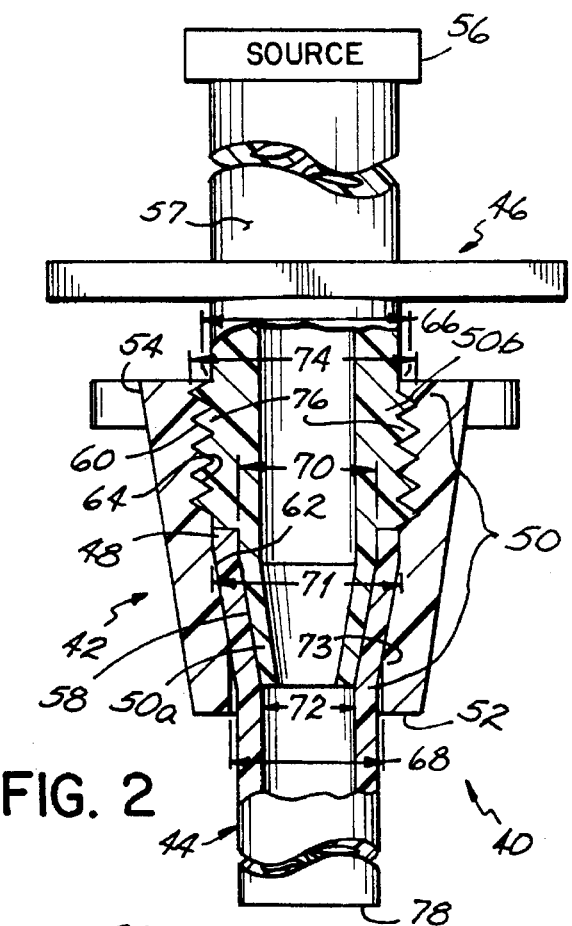
FIG. 2 is a partial cross sectional view of the endotracheal system employing the endotracheal device of the present invention.
Figure 3:
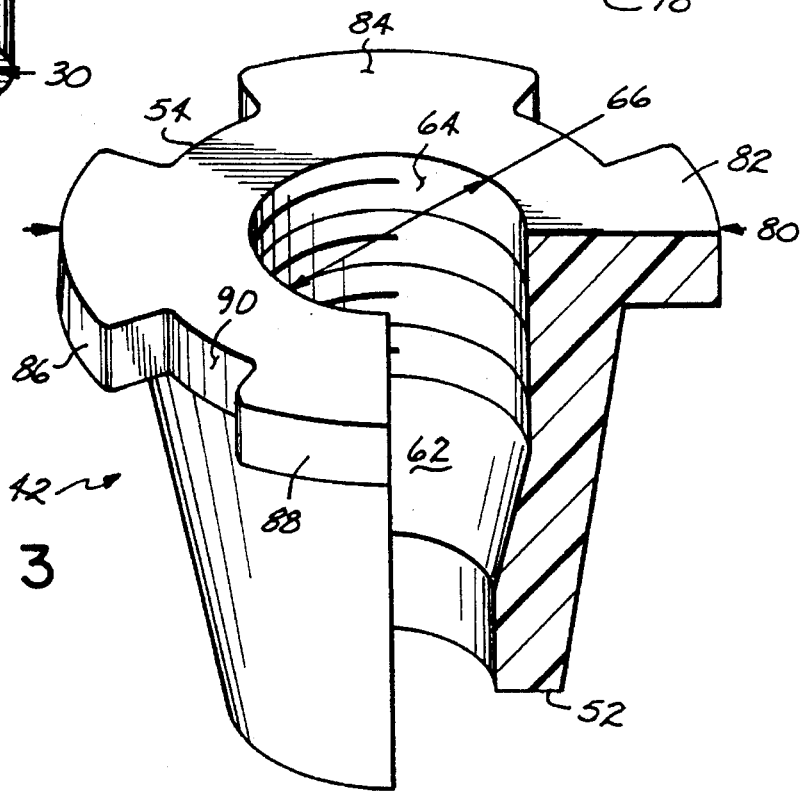
FIG. 3 is a broken-away cross sectional view of the endotracheal device of FIG. 2.

With reference to FIGS. 2 and 3, an endotracheal system 40 is provided with an endotracheal connector device 42 that overcomes the dangers and difficulties encountered with the prior art endotracheal system 10 of FIG. 1. System 40 is comprised of an endotracheal tube 44 and an endotracheal tube adaptor 46. Additionally, system 40 is comprised of endotracheal connector device 42, having a tubular-ring shape, designed to secure a first end 48 of tube 44 to a first end 50 of adaptor 46.

Connector 42 has a first end 52 and a second end 54. First end 52 of connector 42 is adapted to secure first end 48 of endotracheal tube 44 therein, while second end 54 of connector 42 is adapted to secure first end 50 of adaptor 46 therein. A second end 57 of adaptor 46, in turn, is connected to a source 56, such as gas. First end 50 of adaptor 46 is divided into two portions 50a, 50b. First portion 50a is slightly tapered and smooth on the exterior surface 58 while second portion 50b is threaded on the exterior surface 60.

With particular reference to FIG. 3, first end 52 of connector 42 is preferably smooth on its interior surface 62 while second end 54 of connector 42 is threaded on its interior surface 64. Second end 54 of connector 42 has an inner diameter 66 larger than the inner diameter 68 of first end 52 of connector 42 (as shown in FIG. 2) such that connector 42 is tapered.

To secure adaptor 46 to tube 44 tapered, smooth first portion 50a of tubular end 50 of adaptor 46 is inserted into first end 48 of tube 44. Insertion is possible because the inner diameter 70 of first end 48 of tube 44 is slightly larger than the outer diameter 72 of tapered, smooth first portion 50a of first end 50 of adaptor 46. Threaded second portion 50b of first end 50 of adaptor 46, however, does not slide within first end 48 of tube 44 because the outer diameter 74 of second portion 50b of first end 50 of adaptor 46 is larger than inner diameter 70 of first end 48 of tube 44 because of threads 76 located on second portion 50b of first end 50 of adaptor 46 and because second portion 50b of first end 50 of adaptor 46 is not tapered.

Once tapered, smooth first portion 50a of tubular end 50 of adaptor 46 is in first end 48 of tube 44, connector 42 is used to secure adaptor 46 to tube 44. Without the use of connector 42, adaptor 46 might slide out of tube 44 as friction alone is not capable of adequately securing adaptor 46 to tube 44. To secure adaptor 46 to tube 44, second end 78 of tube 44 is first inserted through second end 54 of connector 42 and then through first end 52 of connector 42. Connector 42 is slid up tube 44 until it reaches first end 48 of tube 44. At first end 48 of tube 44, tube 44 is somewhat flared due to the insertion of first end 50 of adaptor 46 therein. Inner diameter 66 of threaded second end 54 of connector 42 is greater than the outer diameter 71 of flared first end 48 of tube 42 such that second end 54 of connector 42 slides past first flared end 48 of tube 44 and cooperatively engages with threads 76 on second portion 50b of first end 50 of adaptor 46. Threaded second end 54 of connector 42 thus screws onto threaded second portion 50b of first end 50 of adaptor 46.

However, threaded second end 54 of connector 42 cannot be threaded past threaded second portion 50b of first end 50 of adaptor 46 because inner diameter 68 of first end 52 of connector 42 is smaller than outer diameter 71 of flared first end 48 of tube 44. Thus, as second end 54 of connector 42 is screwed onto second portion 50b of first end 50 of adaptor 46, first end 52 of connector 42 moves up tube 44 accordingly until inner diameter 68 of first end 52 of connector 42 equals the outer diameter of tube 44 as at 73 (below flared first end 48 of tube 44), and cannot slide past flared first end 48 of tube 42. First end 48 of tube 44 becomes sandwiched or trapped between the inside of first end 52 of connector 42 and the outside of smooth first portion 50a of tubular end 50 of adaptor 46 which was inserted into first end 48 of tube 44.

Therefore, second end 54 of connector 42 secures second portion 50b of first end 50 of adaptor 46 therein via a threading mechanism, while first end 52 of connector 42 secures tube 44 therein as it is unable to pass over first flared end 48 of tube 44 or slide back down tube 44 without unscrewing second end 54 of connector 42 from second portion 50b of first end 50 of adaptor 46. Furthermore, first end 48 of tube 44 is trapped between the inside of first end 52 of connector 42 and the outside of smooth first portion 50a of tubular end 50 of adaptor 46. Accordingly, adaptor 46, which is connected to source 56, is securely connected to tube 44 as connector prevents any movement or the disjunction of adaptor 46 and tube 44. Thus, the risk of source 56 becoming disconnected from system 40 is significantly reduced, if not eliminated.

To facilitate securing connector 42 to first end 50 of adaptor 46, flanges or ridges 82, 84, 86, 88 are located around the exterior surface 90 of connector 42. Flanges 82, 84, 86, 88 extend generally perpendicularly from exterior surface 90 of connector 42 to provide a user (not shown) with an effective manner of grasping and twisting connector 42 for threading onto first end 50 of adaptor 46.

Based on the foregoing description, it will be appreciated that the connector 42 of the present invention provides the ability to easily and securely connect a source 56 to an endotracheal tube 44. The connector 42 has a second end portion 54 that is threaded and can engage with the cooperatively threaded portion 50b of the first end 50 of the adaptor 46. The adaptor 46 is in turn, connected to a source 56. It is therefore quick and easy to screw the connector 42 to the adaptor 46 thereby connecting the source 56 to the system 40. Connecting the adaptor 46 to the connector 42 is further facilitated by the presence of flanges 82, 84, 86, 88.

From the above disclosure of the general principles of the present invention and the preceding detailed description of a preferred embodiment, those skilled in the art will readily comprehend the various modifications to which the present invention is susceptible without departing from the scope of the present invention. For example, the connector may be connected directly to a source capable of being threaded, instead of to an adaptor which in turn is connected to the source. Therefore, we desire to be limited only by the scope of the following claims and equivalence thereof.

What is claimed is:

1. A device to facilitate joining an endotracheal tube to an adaptor connected to a suction or gas source, comprising:

a tubular adaptor having a first threaded end and a second end having a generally smooth outside surface and a tubular connector having opposed ends with an inside diameter for sliding engagement of the connector on an endotracheal tube, one end of the connector being threaded for temporarily locking the connector to the threaded end of said adaptor, and the second end of the connector having a generally smooth inside surface and being slidable on the endotracheal tube so that the endotracheal tube is sandwiched between the smooth inside surface of said second end of the connector and the smooth outside surface of said second end of said adaptor.

2. The device of claim 1 wherein said end of adaptor is tapered to facilitate sandwiching the endotracheal tube between the inside surface of the second end of said connector and the outside surface of said second end of said adaptor.

3. The device of claim 1 further comprising an endotracheal tube.

4. The device of claim 1 wherein said connector has flanges extending generally perpendicularly from an exterior surface of said connector to facilitate grasping and twisting of said connector.

* * * * *